(12) United States Patent
Hartmer (10) Patent No.: US 9,557,297 B2
(45) Date of Patent: Jan. 31, 2017

(54) ALPHA- AND CHI-DIKETONE REACTANTS FOR CHARGE TRANSFER REACTIONS IN MASS SPECTROMETERS

(71) Applicant: Bruker Daltonik GmbH, Bremen (DE)

(72) Inventor: Ralf Hartmer, Hamburg (DE)

(73) Assignee: Bruker Daltonik GmbH, Bremen (DE)

( * ) Notice: Subject to any disclaimer, the term of this patent is extended or adjusted under 35 U.S.C. 154(b) by 777 days.

(21) Appl. No.: 13/667,018

(22) Filed: Nov. 2, 2012

(65) Prior Publication Data

US 2013/0115711 A1    May 9, 2013

(30) Foreign Application Priority Data

Nov. 2, 2011   (DE) .................. 10 2011 117 582

(51) Int. Cl.
*G01N 24/00* (2006.01)
*G01N 27/62* (2006.01)
(Continued)

(52) U.S. Cl.
CPC ........... *G01N 27/62* (2013.01); *H01J 49/0072* (2013.01); *C07C 49/12* (2013.01); *C07C 49/203* (2013.01);
(Continued)

(58) Field of Classification Search
CPC ...... C07C 49/423; C07C 29/143; C07C 49/12; C07C 49/203; C07C 49/437; C07C 2101/14; C07C 2102/42; C07C 49/403; Y10T 436/24; Y10T 436/216; C12P 5/026; C12P 7/26; G01N 27/62; H01J 49/0072; H01L 51/0051
See application file for complete search history.

(56) References Cited

U.S. PATENT DOCUMENTS

| 7,582,862 B2 | 9/2009 | Hartmer |
| 2005/0199804 A1 | 9/2005 | Hunt et al. |
| 2010/0140466 A1* | 6/2010 | Hartmer ............. G01N 33/6848 250/282 |

FOREIGN PATENT DOCUMENTS

| DE | 102005004324 | 8/2006 |
| WO | 2011092515 | 8/2011 |

OTHER PUBLICATIONS

Luckhurst and Orgel, "The electron spin resonance spectra of the 2,2,5,5-tetramethylhexan-3,4-dione and benzil anions", Molec. Phys., 1964, v. 7, No. 3, pp. 297-299 (p. 297).*

* cited by examiner

*Primary Examiner* — Yelena G Gakh
(74) *Attorney, Agent, or Firm* — O'Shea Getz P.C.

(57) ABSTRACT

The invention relates to the use of substances for the production of anions suitable for charge transfer reactions in mass spectrometers, particularly for the fragmentation of multiply positively charged biopolymer ions by electron transfer or for charge reduction by proton transfer. Diketones, particularly α-diketones, are proposed as a newly found class of substances which can be used both for the production of radical anions for electron transfer dissociations (ETD) with a high yield of fragment ions and also for the production of non-radical anions for the charge reduction of multiply charged analyte ions by proton transfer reactions (PTR). These substances have favorable properties in terms of their handling and the associated analytical methods: they are largely nontoxic, cover a favorable range of molecular masses, and their volatility means that they can be stored in unheated containers outside of the vacuum system, which facilitates the refilling of the containers.

16 Claims, 5 Drawing Sheets

3,4-hexanedione    2,3-hexanedione    2,3-heptanedione 2,2,5,5-tetramethylhexane-3,4-dione    2,2,7,7-tetramethyloctane-4,5-dione (51) Int. Cl.
  *H01J 49/00*   (2006.01)
  *C07C 49/12*   (2006.01)
  *C07C 49/203*   (2006.01)
  *C07C 49/403*   (2006.01)
  *C07C 49/437*   (2006.01)

(52) U.S. Cl.
  CPC ............ *C07C 49/403* (2013.01); *C07C 49/437* (2013.01); *C07C 2101/14* (2013.01); *C07C 2102/42* (2013.01); *Y10T 436/24* (2015.01)

Camphorquinone

Figure 6 hex-3-ene-2,5-dione

ALPHA- AND CHI-DIKETONE REACTANTS FOR CHARGE TRANSFER REACTIONS IN MASS SPECTROMETERS

PRIORITY INFORMATION

This patent application claims priority from German Patent Application No. 10 2011 117 582.6 filed on Nov. 2, 2011, which is hereby incorporated by reference in its entirety.

FIELD OF THE INVENTION

The invention relates to substances for the production of anions suitable for charge transfer reactions in mass spectrometers, particularly for the fragmentation of multiply positively charged biopolymer ions by electron transfer or for charge reduction by proton transfer.

BACKGROUND OF THE INVENTION

Nowadays, the sequences of the basic building blocks of biopolymers and their post-translational modifications (PTM) are identified predominantly with the aid of tandem mass spectrometers. In the following, peptides and proteins as biopolymers are dealt with in particular, although the invention should not be limited to these. For example, oligosaccharides are a further group of biopolymers whose monomeric basic units, the sugar molecules, can be linked with each other in linear or in branched form. A key technology for these investigations is the fragmentation of the biopolymer ions in the mass spectrometer. There are two fundamentally different types of fragmentation: ergodic fragmentation and non-ergodic, electron-induced fragmentation, for each of which several methods are known. The electron-induced fragmentation of the peptide or protein ions is complementary to the ergodic fragmentation, firstly because it cleaves at different points of the amino acids within the chain of amino acids, and secondly because it does not remove the side chains of the post-translational modifications during fragmentation, as is the case with ergodic fragmentation. By comparing the fragment ion spectra obtained ergodically with those obtained non-ergodically, the sequences as well as the mass and position of the modifications can be read.

A relatively simple electron-induced fragmentation method is electron transfer dissociation. It is possible to use specific types of negative reactant ions to cleave multiply positively charged biopolymer ions, particularly peptide or protein ions, by the transfer of an electron ("ETD"=electron transfer dissociation). The reactant ions are usually radical anions of the form $M^{\cdot-}$ of a molecule M; these radical anions easily give up electrons. See U.S. Published Patent Application 2005/0199804 A1 (D. F. Hunt et al.) and German Patent DE 10 2005 004 324 B4 (R. Hartmer and A. Brekenfeld). Both documents describe how multiply charged positive peptide or protein ions are fragmented by reactant ions with this method. Electron transfer dissociation is a special form of the general group of charge transfer reactions.

A second form of charge transfer reaction which is often used is the reaction between multiply positively charged analyte ions and non-radical negatively charged ions of the form $(M-H)^-$ or $(M+H)^-$, which can be used to reduce the number of respective charges on the positive analyte ions ("PTR"=proton transfer reactions, also called "charge stripping"). In favorable cases, the non-radical anions required for this can be obtained in electron attachment ion sources from the same substances that are used for the production of radical anions for ETD (see U.S. Pat. No. 7,582,862 B2) by changing the operating conditions. The charge reduction enables highly charged analyte ions to be converted into less highly charged ions in order to reduce the complexity of the mass spectra from mixtures of many different highly charged analyte ions and to produce favorable biopolymer ions for electron transfer dissociation.

The reactions for electron transfer dissociation (ETD) and also for charge reduction by proton transfer (PTR) take place in reaction cells, in which both positive and negative ions can be stored. These can be two-dimensional RF ion traps with pseudopotential barriers at the ends, for example, but also three-dimensional RF ion traps. These reaction cells are usually filled with a damping gas, in which the ion motions are thermalized. Mass spectrometers with both types of reaction cells are commercially available and are known to those skilled in the art. The positive analyte ions and the negative reactant ions are generally introduced sequentially into the ion traps and mixed there. The reactions can then occur without any further assistance.

U.S. Published Patent Application 2005/0199804 ("'804 Application") explains that substances for the formation of ETD reactant ions can be found in the group of polycyclic aromatic hydrocarbons (polyaromatic hydrocarbons). Specifically, the substances anthracene, naphthalene, fluorene, phenanthrene, pyrene, fluoranthene, chrysene, triphenylene, perylene, acridine and others are named. With some of these substances, however, the electron attachment ion source always supplies non-radical anions of the form $(M-H)^-$ also, as can be seen in Table 1 of the '804 Application, and these produce undesirable proton transfer reactions here. Thus not all of these polycyclic aromatic compounds are equally advantageous for ETD. Disadvantageous, on the whole, for all polycyclic aromatic compounds is the fact that they have very low vapor pressures. To avoid condensation in relatively cool supply lines, it is therefore necessary to keep these substances in a heated vessel close to the electron attachment ion source, which must also be heated, in the interior of the mass spectrometer. This makes refilling complicated, and may even have to be done by the manufacturer's service staff. Although it would be possible to heat all the supply lines between a heated vessel external to the vacuum system and the electron attachment ion source, it is extremely difficult to uniformly heat supply lines that pass through the wall of the vacuum system.

High ETD effectiveness of the anions of a substance means here that, on the one hand, a high yield of fragment ions is achieved and, on the other hand, no significant proportion of proton-transfer reactions occurs. According to the '804 Application, fluoranthene is particularly ETD effective in this sense.

Published U.S. Patent Application U.S. 2010/0140466 A1, incorporated herein by reference, proposes aliphatic substances with electron affinities between 0.3 and 0.8 electron volts, particularly 1,3,5,7-cyclooctatetraene (m=104.15 Da, EA=0.550 eV); trichloroethene, (m=131.39 Da; EA=0.400 eV), tetrachloroethene (m=165.83 Da; EA=0.64 eV) and 2,3-butanedione (m=86.09 Da; EA=0.69 eV). The advantage of these substances is that their higher vapor pressures mean that they can be kept in an unheated vessel external to the mass spectrometer, which facilitates the refilling. 1,3,5,7-cyclooctatetraene, which was preferred initially, has turned out to be not particularly suitable for some types of reaction cells because in these cells it very quickly loses the electrons, which are only weakly bound.

As the best substance in this group, 2,3-butanedione provides good yields of fragment ions of the multiply positively charged analyte ions. The ETD effectiveness approaches that of fluoranthene.

2,3-butanedione also has disadvantages, however. Firstly, it is a respiratory and eye irritant with hotly debated toxicity (approved as butter flavor in Europe, although it is known to cause pulmonary diseases), and therefore its use is neither simple nor without risk, precisely because of its otherwise favorable vapor pressure. Secondly, it has a very low molecular mass of only 86 atomic mass units. If it is to be stored in an RF storage cell, the RF voltage must be lowered to such an extent that heavy positive ions are lost because of the limited mass range of all such storage cells. And thirdly, the electron attachment ion source which is used to produce the anions from butanedione cannot be switched to also produce the non-radical anions which can be used for proton-transfer reactions (PTR) for the charge reduction. The search for further, favorable substances for the ETD is thus not concluded.

PCT Application WO 2011/092515 discloses substances with Franck-Condon factors between 0.1 and 1.0, and electron affinities between 0.1 and 150 kJ/mol (1.55 eV). A list of more than 90 substances is provided, starting with 1,3- and 1,4-dicyanobenzol. The list contains both aromatic and aliphatic compounds from very different substance classes.

The electron affinity (EA) is the energy which must be used to remove the electron from the radical anion again, i.e., the binding energy of the added electron. This binding energy must not be too low because, otherwise, the substance hardly accepts any electrons, on the one hand, and, having accepted an electron, the anions easily lose it again, on the other hand. The binding energy must not be too high either, however, because otherwise the positive biopolymer ions cannot detach and attract the electron, i.e., cannot affect the electron transfer.

The aliphatic ETD substances listed above were taken from the extensive NIST database for organic substances (webbook.nist.gov), which represents one of the most complete databases for physical chemistry data of organic chemical substances. In its table of organic substances with known electron affinity, only around 200 substances in total are listed in the range from EA=0.3 to 0.8 eV, and few of them are suitable aliphatic compounds, whereas nearly all the polycyclic aromatic compounds from the '804 Application can be found there. It must be assumed that for a large majority of organic substances, especially aliphatic substances, the electron affinities are not known, so a search in the specialist literature promises little success.

There is a need of providing starting substances for the production of anions for charge transfer reactions, particularly substances for the production of radical anions for electron transfer dissociation with high ETD efficiency which do not have the disadvantages observed with the ETD reagents known up to now.

SUMMARY OF THE INVENTION

For the production of ETD reactant ions, and also for the production of PTR reactant ions, the substances from the substance class of the diketones may be used, preferably α diketones, whose molecular masses are heavier than 2,3-butanedione. Substances of this class can uniformly cover the range from m/z=100 Da to m/z=200 Da and higher, and therefore the mass m/z of the reactant ions can be matched to the analytical task by selecting the appropriate diketone. Most of these substances are nontoxic; some are used as fragrances in perfumes. Their vapor pressures are two to three orders of magnitude higher than those of polycyclic aromatic compounds, so they can be kept in vessels outside of the mass spectrometer. From at least some of these substances, non-radical anions for proton transfer reactions (PTR) can be produced in appropriately operated electron attachment ion sources by a simple change to the operating conditions.

Hence, diketones, particularly α-diketones, are proposed as a newly class of substances that can be used both for the production of radical anions for electron transfer dissociations (ETD) with a high yield of fragment ions and also for the production of non-radical anions for the charge reduction of multiply charged analyte ions by proton transfer reactions (PTR). These substances have favorable properties in terms of their handling and associated analytical methods: they are largely nontoxic, cover a favorable range of molecular masses, and their volatility means that they can be stored in unheated containers outside of the vacuum system, which facilitates the refilling of the containers. It can be expected that certain chiral diketones are even able to stereoselectively fragment analyte ions with stereogenic centers.

Many substances belong to these classes of substances. Proposed as examples are 2,3-pentanedione ($H_3C$—CO—CO—$CH_2$—$CH_3$; m=100 Da), 3,4-hexanedione ($H_3C$—$CH_2$—CO—CO—$CH_2$—$CH_3$, m=114 Da), 2,3-hexanedione ($H_3C$—CO—CO—$CH_2$—$CH_2$—$CH_3$, m=114 Da), 3,4-heptanedione (m=128 Da), 2,3-heptanedione (m=128 Da), 2,3-octanedione (m=142 Da), 3,5,5-trimethyl-1,2-cyclo-hexanedione (m=154 Da), 2,2,5,5-tetramethylhexane-3,4-dione (m=170 Da) and 2,2,7,7-tetramethyloctane-4,5-dione (m=196 Da). These substances only examples, however; many other diketones are candidates for the production of successful ETD anions.

It is expected, furthermore, that chiral analyte ions can also be selectively fragmented with chiral reactant ions, for example produced from camphorquinone (m=166 Da). This would provide a tool for the stereoselective analysis of substances with one or more stereogenic centers.

These and other objects, features and advantages of the present invention will become more apparent in light of the following detailed description of preferred embodiments thereof, as illustrated in the accompanying drawings.

BRIEF DESCRIPTION OF THE DRAWING

FIG. 8 is a schematic representation of an ion trap mass spectrometer for carrying out ETD, with an electrospray ion source 1, 2 for the production of the multiply positively charged analyte ions, an electron attachment ion source 8 for the production of the negatively charged reactant ions (radical anions), and end cap electrodes 11, 13 and ring electrode 12 of a 3D ion trap, which serves as the reaction cell for the ETD. The ion guide 9 has the form of a multipole rod system and can guide both positive and negative ions to the ion trap. According to the Prior Art, the starting substance for the production of the radical anions is in a heated container 18 close to the ion source 8; however, the use of volatile starting substances according to this invention makes it possible to install the substance vessel 19, through which methane gas from a supply tank 20 flows, outside of the vacuum system without heating;

DETAILED DESCRIPTION OF THE INVENTION

The '804 Application discloses that the aromatic rings in polycyclic aromatic compounds are groups which are suitable for an electron attachment with favorable electron affinities. Due to fundamental considerations, substances with double bonds, and polyenes in particular, seem to be particularly favorable starting substances. Polyenes are organic compounds that contain two or more carbon-carbon double bonds. However, the search for aliphatic substances with double bonds which are particularly suitable for ETD has not so far been successful, apart from those substances listed in the introduction and some of the substances stated in PCT Application WO 2011/092515 A1.

The information on the electron affinities of organic substances that can be found in the literature is largely insufficient. It has been therefore unclear which other chemical groups within the molecules may be responsible for a favorable electron attachment. For the aliphatic compounds, it was found that the group of two adjacent ketones, as occurs within the 2,3-butanedione molecule, may be responsible for this sufficiently strong, yet still sufficiently reactive, electron attachment in a similar way to the aromatic rings. Substances with adjacent, so-called "vicinal" ketone groups are termed "α-diketones". No α-diketones are included in the long list of substances which is given in PCT Application WO 2011/092515 A1 cited above.

Surprisingly it turned out that all the α-diketones investigated so far are eminently suitable for the production of radical anions for the process of electron transfer dissociation, and at least as suitable as the only substance investigated so far, 2,3-butanedione.

It is therefore proposed to use starting substances from the substance class of diketones for the production of ETD reactant ions, particularly the α-diketones, whose molecular masses, at m≥100 atomic mass units, are heavier than 2,3-butanedione. Many such α-diketones are available, which can cover the range from m/z=100 Da to m/z=200 Da and higher very uniformly; and therefore the mass m/z of the reactant ions can be matched to the analytical task by the selection of the diketone.

The following substances are briefly presented here as a small number of examples from the many α-diketones, for which a few structural formulas are shown in FIGS. 1-6:

2,3-pentanedione ($H_3C-CO-CO-CH_2-CH_3$; m=100 Da; boiling point 110 to 112° C.) is a nontoxic, yellow liquid with pungent smell that has been detected in many foods such as peas, tomatoes, potatoes, milk, meat and nuts. The structural formula corresponds to the general representation in FIG. 2 with n=0 and m=1.

Figure 1:
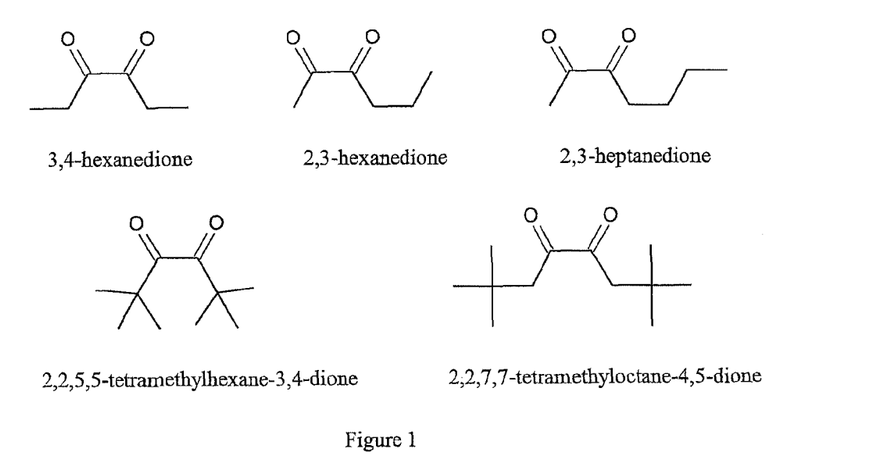
FIG. 1 shows the structural formulas of some alkane-α-diketones.
Figure 2:
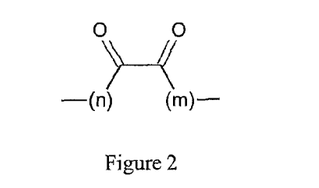
FIG. 2 gives the general structural formula for linear alkane-α-diketones, where (n) with n≥0 and (m) with m≥0 represent the lengths of the alkyl groups.
Figure 9:
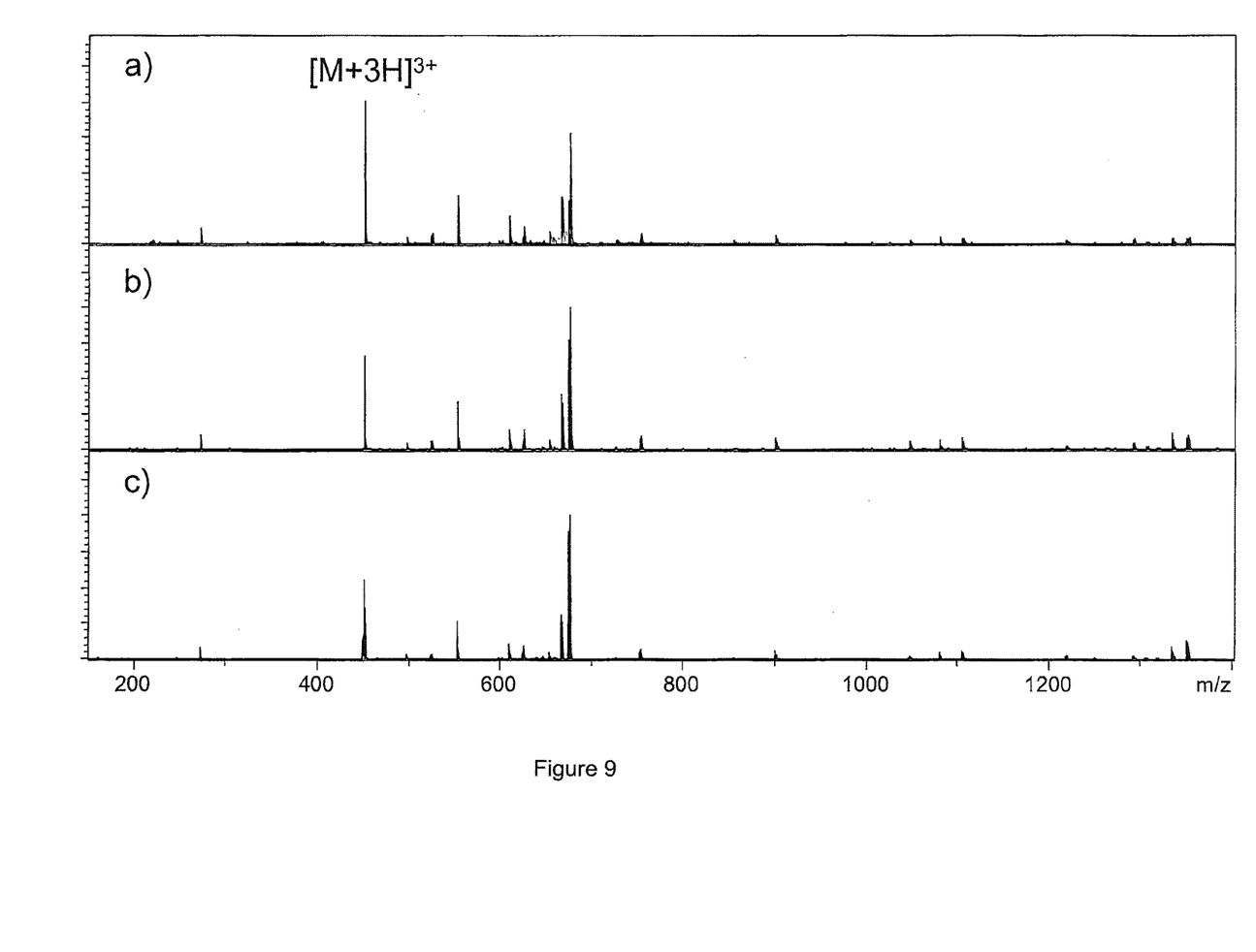
FIG. 9 depicts measured fragment ion spectra from "substance P", which were obtained a) using fluoranthene (m=202 Da), b) 3,4-hexanedione (m=114 Da), and c) 2,3-heptanedione (m=128 Da). Until now, fluoranthene has been considered the best candidate for ETD reactions; the fragmentations by the two diketones are practically equivalent to that of fluoranthene. Substance P is a peptide which is often used as a test substance for ETD. The y-axis has the same scale in all three spectra.
Figure 10:
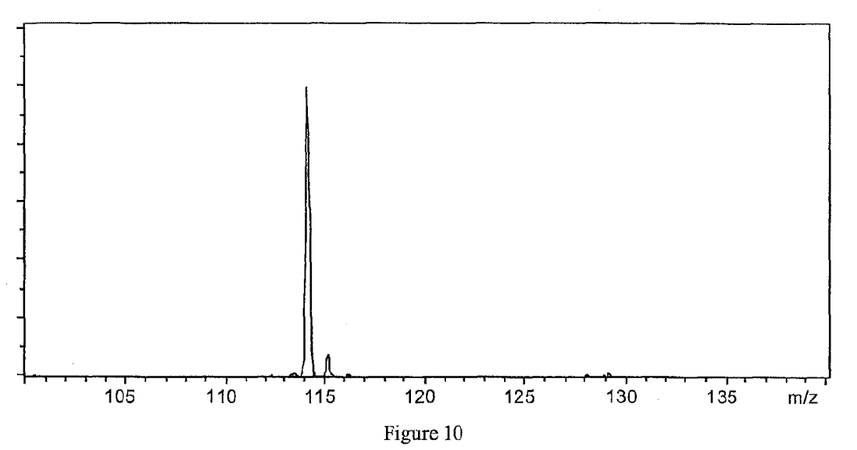
FIG. 10 shows the formation of radical anions $M^{\cdot-}$ of mass m/z=114 Da from 2,3-hexanedione (m/z=114 Da) in a mass spectrum.
Figure 11:
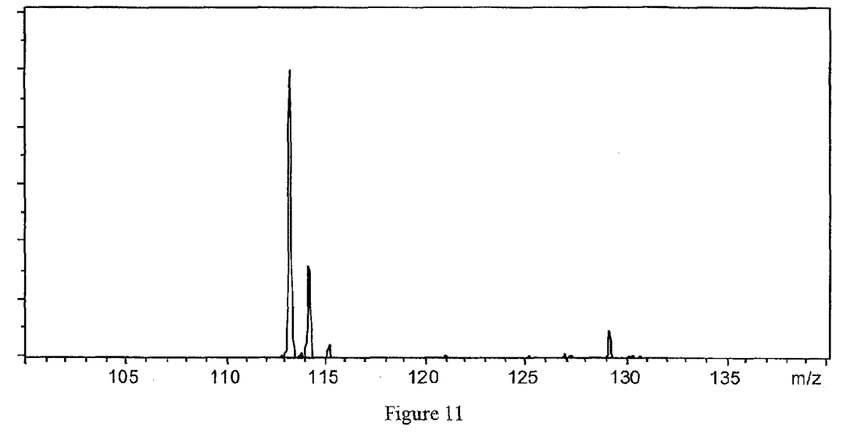
FIG. 11 represents a mass spectrum of the non-radical anions $(M-H)^-$ (m/z=113 Da), which were obtained in the same electron attachment ion source by changing the operating conditions. It is a deprotonated anion starting from 2,3-hexanedione, with a by-product at m/z=129 Da. The by-product is produced in the electron attachment ion source, which operates with methane as the thermalization gas, from a radical-radical reaction between a methyl radical and a radical anion from hexanedione. Both the by-product and the non-radical anion are effective as a reactant ion for PTR.

Although the two α-diketones 3,4-hexanedione (m=114 Da) and 2,3-hexanedione (m=114 Da), both shown in FIG. 1, are flammable, they are nontoxic, in contrast to the highly toxic 2,5-hexanedione, where the two ketone groups are not adjacent. 3,4-hexanedione is a slight skin irritant, so 2,3-hexanedione, which is occasionally used in perfumes, is preferred. As is shown in FIGS. 10 and 11, in electron attachment ion sources they produce as well radical anions of the form $M^{\cdot-}$ with ion mass m/z=114 Da as non-radical anions of the form $(M-H)^-$ with ion mass m/z=113 Da in a controllable way. In FIG. 9, spectrum b) shows the fragment ions which were obtained by the radical anion of 2,3-hexanedione by electron transfer dissociation.

3,4-heptanedione (m=128 Da) and 2,3-heptanedione (m=128 Da), the latter also shown in FIG. 1, are also two α-diketones without any special hazard designation, except for their flammability. They are also used in perfumes. Both are suitable for the production of radical anions of mass 128 Da for ETD and also for non-radical anions of mass 127 Da for PTR. FIG. 9 (c) depicts the fragment ion spectrum which has been produced from substance P by ETD with anions from 2,3-heptanedione.

The series can be continued to heavier unbranched or branched alkane-α-diketones, for example 2,3-octanedione (m=142 Da) or even to 2,2,7,7-tetramethyloctane-4,5-dione (FIG. 1; m=196 Da).

Figure 3:
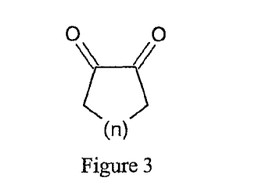
FIG. 3 represents the general structural formula for cyclic α-diketones, where (n) with n≥0 represents the number of carbons in the enclosed chain.
Figure 4:
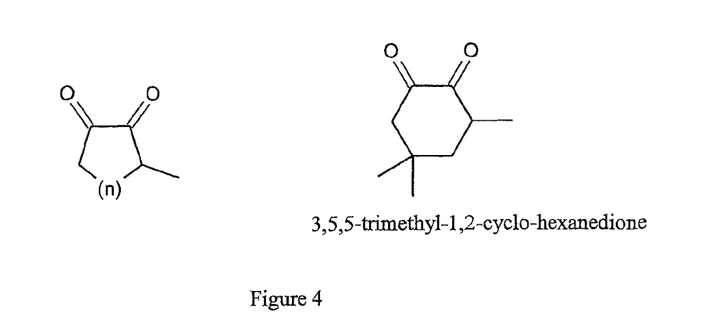
FIG. 4 shows a general structural formula for branched cyclic α-diketones, where (n) with n≥0 represents the lengths of the alkyl group, together with a specific example.
Figure 5:
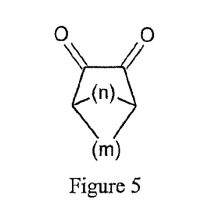
FIG. 5 gives a general structural formula for multiply cyclic α-diketones, where (n) with n≥0 and (m) with m≥0 represent the lengths of the alkyl groups.
Figure 6:
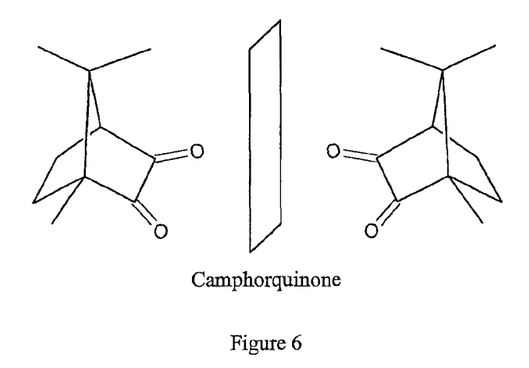
FIG. 6 shows the two enantiomers of camphorquinone, a bicyclic α-diketone.

It is also possible to use cyclically bound α-diketones, however. FIG. 3 illustrates the general structural formula for unbranched cyclic α-diketones, FIG. 4 the structural formula for branched α-diketones, such as 3,5,5-trimethyl-1,2-cyclohexanedione (m=154 Da), which is also depicted in FIG. 4. A general structural formula for bicyclic α-diketones is shown in FIG. 5. As an example of this, the two enantiomers of camphorquinone (m=166 Da) are shown in FIG. 6; both are also nontoxic.

The electron affinities of some β-diketones are described in an overview article by P. Kebarle (Chem. Rev. 1987, 87, 513-534). These electron affinities, 1.44 eV for malonic acid anhydride and 1.21 eV for phthalic acid anhydride, are, however, above the favorable range, which extends to around 0.8 eV. Although two cyclo-β-diketones are contained in the lists of the above-cited PCT Application WO 2011/092515 A1, the β-diketones seem to be not very favorable substances for the generation of anions for ETD.

Figure 7:
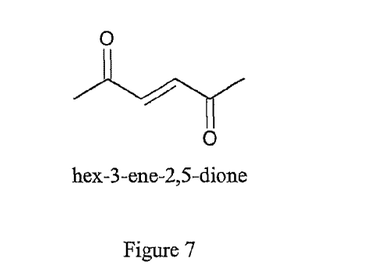
FIG. 7 shows hex-3-ene-2,5-dione, a relatively simple χ-diketone with a C=C double bond between the two ketone groups.

In some contrast, χ-diketones, which have a C=C double bond between the two ketone groups, such as hex-3-ene-2,5-dione (FIG. 7), may also be good as ETD substances; the invention should therefore not be limited to α-diketones only, but include particularly also the χ-diketones.

The substances named individually are only examples, however; many further diketones are candidates for the production of successful ETD radical anions based upon the present invention. Most of these substances are nontoxic, in contrast to 2,3-butanedione.

It is particularly advantageous that the vapor pressures of most diketones are two to three orders of magnitude higher than those of the polycyclic aromatic compounds. They are usually greater than 0.1 pascal at standard temperature. They can therefore be kept in unheated vessels outside of the mass spectrometer and be entrained by a thermalization gas, such as methane, into the electron attachment ion source. As far as has been investigated, these substances also supply nonradical anions for proton transfer reactions (PTR) in appropriately operated electron attachment ion sources by setting appropriate operating conditions.

Detailed investigations on the course of the electron transfer dissociation by the research group working with S. McLuckey (H. P. Gunawardena et al.; J. Am. Chem. Soc. 2005, 127, 12627-12639) and by D. Simmons (Chem. Phys. Letters 2010, 484, 81-95) have come to the conclusion that, before the electron transfer, a joint transition complex is formed, which comprises the reactant ion and the biopolymer ion. The formation of the complex is many times slower than the electron transfer itself and determines the temporal course of the reaction. If these results prove to be conclusive, it must be expected that steric hindrances can occur during the formation of the complexes if the reactant ions and the biopolymer ions have the appropriate form. The steric hindrances and preferences may then be utilized analytically, for example to investigate the chirality of biopolymer ions.

In contrast to the substance class of the polyaromatic hydrocarbons, which is the best investigated class for ETD so far, the substance class of the diketones allows carbon atoms which have a chiral center that includes four different substituents to be specifically incorporated into the alkyl skeleton of the linear or cyclic diketones. Enantiomers (molecules with minor symmetry) or diastereomers (molecules with several chiral centers) are special forms of chiral molecules. Those skilled in the art are familiar with ways of synthesizing diketones with the desired chirality.

Proteins formed wholly or partially from non-naturally occurring D-amino acids are particularly interesting as pharmacological active agents. The high degree of effectiveness of such proteins is based in part on the fact that the enzymatic degradation of the protein in vivo proceeds more slowly due to the incorporated D-amino acids. The analysis of the stereo information of the carbon atoms of the amino acids is interesting for the characterization of such non-naturally occurring proteins.

It is to be expected that chiral, and particularly enantiomeric, reactant ions, pure or enriched, make it possible to distinguish between proteins with naturally occurring L-amino acids and those with non-naturally occurring D-amino acids. The yields of the electron transfer dissociation with enantiomeric reactant ions will probably differ depending on the R-enantiomer or S-enantiomer because, in the transition complex of reactant ion and protein ion, the attachment of the reactant ion to a specific side is sterically hindered. If one of the two enantiomers of the amino acid is present in the protein under investigation, the intensity of the fragment ion will be different to similarly occurring fragment ions of all the other amino acids which are present.

In comparison to the proteins, which with few exceptions are based on the naturally occurring L-amino acids, the number of carbons which can occur in the R or S configuration is much larger for natural sugar molecules. A single reduced aldohexose sugar molecule, for example, has, in the open form, four carbons with so-called stereogenic centers. Most of the possible diastereomers also occur in nature.

According to recent investigations by L. Hang and C. Costello (J. Am. Soc. Mass Spectrom. 2011, 22; 997-1013), electron transfer dissociation of multiply positively charged oligosaccharides provide useful structural information on the sugar molecules to supplement the ergodic collision-induced fragmentations which have usually been used to date. The number of so-called ring splittings, which are particularly advantageous for the assignment of individual sugar molecules, is particularly large with the electron transfer dissociation of oligosaccharides with magnesium cations as the adduct ion. Reactant ions originating from fluoranthene, which does not have any chiral carbon, were used in the investigations mentioned here. Thus no stereoselective electron transfer dissociation may be observed.

It is to be expected, however, that here also chiral, and particularly enantiomeric, reactant ions make it possible to distinguish between diastereomeric sugar molecules which are incorporated into the oligosaccharides. The yields of the electron transfer dissociation with enantiomeric reactant ions will probably also vary here, depending on the R-enantiomer or S-enantiomer, because in the transition complex of reactant ion and oligosaccharide, the attachment of the reactant ion to a specific side is sterically hindered. If one of the possible sugar diastereomers is present in the oligosaccharide under investigation, the intensity of the fragment ion will be different to the also occurring fragment ions of all the other sugar molecules.

A embodiment of the invention therefore includes using chiral, and particularly enantiomeric or diastereomeric, diketone ions for the electron transfer dissociation. An example is provided by the radical anion of camphorquinone (FIG. 6). Enantiomeric camphorquinones can be produced in only a few reaction steps; those skilled in the art are familiar with the ways of doing this.

Auxiliaries are substances which affect the ratio of reaction products in a chemical reaction. A well-known example is the so-called Evans auxiliary, a chiral oxazolidinone named after the Nobel Laureate D. Evans, which leads to an enantio-selective α-alkylation of the ester of carboxylic acid. A further chiral auxiliary is the Helmchen auxiliary, named after the chemist C. Helmchen, which is obtained from naturally occurring camphor. Most chiral auxiliaries are derived from naturally occurring chemical substances and are therefore often easy to obtain.

Stereoselective electron transfer dissociations or proton-transfer reactions in mass spectrometers which are controlled by a chiral reactant ion have not yet been described in the literature. But chiral reactant ions make it possible to specifically control the reactions between reactant ions and biopolymer ions so that the stated reactions proceed stereoselectively.

Figure 8:
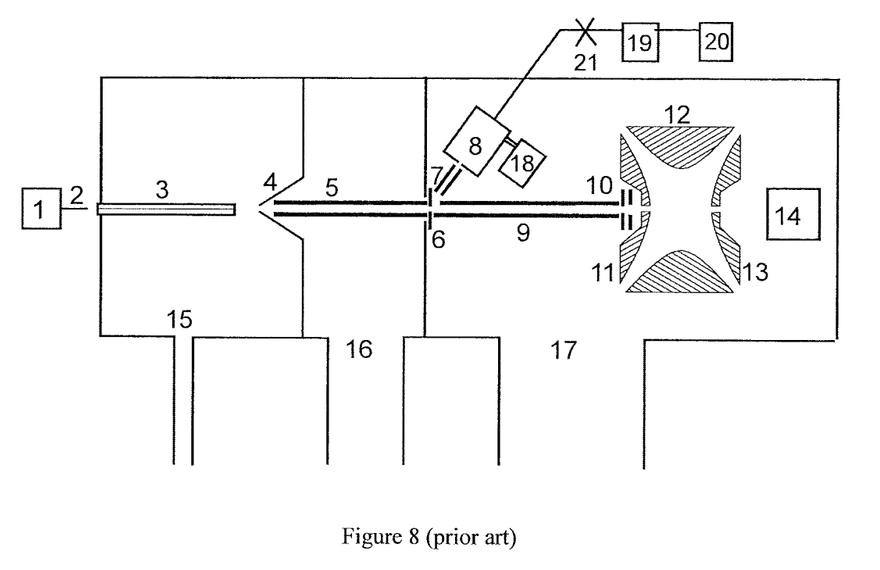

An example of an ion trap mass spectrometer for carrying out electron transfer dissociation is shown schematically in FIG. 8. Here, an electrospray ion source 1 with a spray capillary 2 outside the mass spectrometer is used to ionize the biopolymers. It will be assumed here that a mixture of digest peptides of a larger protein is to be analyzed. The ions are guided in the usual way through an inlet capillary 3 and a skimmer 4 with the ion guides 5 and 9 through the pressure stages 15, 16, 17 to the 3D ion trap with end cap electrodes 11 and 13 and ring electrode 12, where they are captured. The ion guides 5 and 9 comprise parallel rod pairs, across which the phases of an RF voltage are alternately applied. They can take the form of a quadrupole, hexapole or octopole rod system.

A first mass spectrum, obtained by resonant excitation of the ions with mass-selective ejection with measurement of the ejected ions in the ion detector 14, provides an overview of the digest peptides, since practically only molecular ions, albeit in different charge states, and no fragment ions are formed in the electrospray ion source. If it is now intended to analyze one or more peptides to determine their sequence of amino acids, the triply charged ions of this peptide, for example, are isolated by normal mechanisms; in other words the ion trap is first overfilled and then all ions which are not triply charged ions of this peptide are ejected from the ion trap. The triple charge is recognized by the spacing of the isotope lines; for triply charged ions this is exactly ⅓ of an atomic mass unit. If triply charged ions are not available in sufficient numbers, then ions with a different charge state can also be used.

These now isolated multiply charged ions are decelerated into the center of the trap by a short delay of a few milliseconds by the ever-present collision gas. The negatively charged ions are then added. These ions are generated in a separate ion source 8 for negative chemical ionization (electron attachment ion source) and guided via a small ion guide 7 to the ion guide 9. Ion guides of this type can transmit both positive and negative ions. The negative reactant ions are introduced into the rod-shaped octopole ion guide 9 through two shortened rods, and thus reach the ion trap, where they are stored in the usual way through an injection lens 10. Here they react immediately (within a few milliseconds) with the positive ions.

The low vapor pressure of most substances used up to now for the production of radical anions meant they had to be kept in a vessel 18 which may be heated to between 50° and 250° Celsius, and which was installed close to the electron attachment ion source 8, which was also heated. In most cases, there were no valves at all, so it was not possible to close off the substance vessel. As already explained in the introductory section, this arrangement has disadvantages because it means that the substances are quickly consumed and the vacuum system of the mass spectrometer must be vented each time it is refilled with the substance. Extremely rapid consumption may only be prevented by switching off the heating. Being able to use substances with a higher vapor pressure for ETD means that the substance, for example the 2,3-heptanedione, can now be kept in a vessel 19 outside the mass spectrometric vacuum system. This makes refilling relatively easy. In addition, the vessel 19 can now be kept at room temperature, which removes the difficulty of having to pass a heated gas line through the unheated walls of the vacuum system. This vessel 19 can, for example, be flushed directly with methane from a supply tank 20, with the methane being used as the thermalization gas for the electron attachment ion source. The methane entrains sufficient substance for the production of radical anions. It is also easily possible to equip the gas line with a valve 21 for closing the line so that the supply of the substance, and also of the thermalization gas, can be interrupted if required. If several vessels and several valves are installed, it is possible to switch between several starting substances, for example substances with different masses.

The fragment ions formed during the process of electron transfer dissociation sometimes remain associated with each other and thus form unstable radical cations, but these do not decompose immediately. It is therefore favorable to apply a weak dipolar alternating excitation voltage for a resonant excitation of these radical cations across the two end caps 11, 13 of the ion trap. The frequency for this alternating excitation voltage can be calculated from the known mass of these radical cations and their known charge. This excitation voltage causes these radical cations to quickly decompose, a process which requires only relatively weak collisions, and which increases the yield of the desired species of fragment ion.

The non-radical anions of mass m=127 Da produced from the 2,3-heptanedione in the electron attachment ion source under changed operating conditions can be successfully used for a charge reduction by proton transfer reactions. Even if they cannot be extracted from the ion source with completely clean separation from the radical anions, they are suitable for PTR because charge reduction and electron transfer dissociation are usually carried out simultaneously anyway in order to save time. The ratio of the two ionic species can be set within wide limits by the extraction voltage at the ion source.

With the knowledge that substances with higher vapor pressures and a wide range of molecular masses can also be used as starting substances for the production of radical anions for ETD, those skilled in the art can take further measures which facilitate the handling of the mass spectrometer or the carrying out of the analytical methods.

While the invention has been shown and described with reference to a number of embodiments thereof, it will be recognized by those skilled in the art that various changes in form and detail may be made herein without departing from the spirit and scope of the invention as defined by the appended claims.

Although the present invention has been illustrated and described with respect to several preferred embodiments thereof, various changes, omissions and additions to the form and detail thereof, may be made therein, without departing from the spirit and scope of the invention.

What is claimed is:

1. A method for reacting analyte ions with anions in a mass spectrometer, comprising:
   producing multiply positively charged analyte ions from a substance that is a biopolymer using a first ion source, producing the anions from a substance that is one of an α-diketone and a χ-diketone having a molecular mass m greater than or equal to 100 Dalton using a second ion source,
   guiding and introducing the multiply positively charged analyte ions and the anions into a reaction cell of the mass spectrometer where the multiply positively charged analyte ions and the anions are brought together in order to induce charge transfer reactions.

2. The method of claim 1, where the step of producing anions comprises producing radical anions from the substance that is one of an α-diketones or a χ-diketone, and further comprising using the radical anions for electron transfer dissociation of the multiply positively charged analyte ions in the mass spectrometers.

3. The method of claim 1, where the step of producing anions comprises producing non-radical anions from the substance that is one of an α-diketones or a χ-diketone, and further comprising using the non-radical anions for proton transfer reactions of the multiply positively charged analyte ions in the mass spectrometers.

4. The method of claim 1, wherein the substance that is one of an α-diketones -or a χ-diketone has a vapor pressures above about 0.1 pascal at standard temperature.

5. The method of claim 1, wherein the substances belong to the substance class of the open-chain alkane α-diketones.

6. The method of claim 1, wherein the substances belong to the substance class of the cyclic α-diketones.

7. The method of claim 1, wherein the keto groups of the substances are linked by one or more C=C double bonds.

8. The method of claim 1, wherein at least one carbon atom in the alkane skeleton of the substances contains four different substituents, whereby formation of enantiomers or diastereomers ensues.

9. The method of claim 1, wherein the substance that is an α-diketone is selected from the group consisting of 2,3-pentanedione, 3,4-hexanedione, 2,3-hexanedione, 3,4-heptanedione, 2,3-heptanedione, 2,3-octanedione, 3,5,5-trimethyl-1,2-cyclo-hexanedione, 2,2,5,5-tetramethylhexane-3,4-dione, and 2,2,7,7-tetramethyloctane-4,5-dione.

10. The method of claim 1, wherein the reaction cell is one of a two-dimensional RF ion trap and three-dimensional RF ion trap.

11. The method of claim 1, wherein the biopolymer is chosen from one of peptides, proteins, and oligosaccharides.

12. The method of claim 1, wherein the multiply positively charged analyte ions and the anions are reacted in order to at least one of (i) fragment the multiply positively charged analyte ions by electron transfer and (ii) charge-reduce the multiply positively charged analyte ions by proton transfer.

13. A method for reacting analyte ions with anions in a mass spectrometer, comprising:

producing multiply positively charged analyte ions from a substance that is a biopolymer using a first ion source, producing the anions from a substance that is a diketone having a molecular mass m greater than or equal to 100 Dalton, wherein keto groups of the substance that is a diketone are linked by one or more C=C double bonds using a second ion source, guiding and introducing the multiply positively charged analyte ions and the anions into a reaction cell of the mass spectrometer where the multiply positively charged analyte ions and the anions are brought together in order to induce charge transfer reactions.

14. The method of claim 13, wherein the substance that is a diketone is hex-3-ene-2,5-dione.

15. A method for reacting analyte ions with anions in a mass spectrometer, comprising:

producing multiply positively charged analyte ions from a substance that is a biopolymer using a first ion source, producing the anions from a substance that is a diketone having a molecular mass m greater than or equal to 100 Dalton using a second ion source, wherein at least one carbon atom in an alkane skeleton of the substance that is a diketone contains four different substituents, whereby formation of enantiomers or diastereomers ensues, and guiding and introducing the multiply positively charged analyte ions and the anions into a reaction cell of the mass spectrometer where the multiply positively charged analyte ions and the anions are brought together in order to induce charge transfer reactions.

16. The method of claim 15, wherein the substance that is a diketone is camphorquinone.

* * * * *

UNITED STATES PATENT AND TRADEMARK OFFICE
CERTIFICATE OF CORRECTION

| | | |
|---|---|---|
| PATENT NO. | : 9,557,297 B2 | Page 1 of 1 |
| APPLICATION NO. | : 13/667018 | |
| DATED | : January 31, 2017 | |
| INVENTOR(S) | : Ralf Hartmer | |

It is certified that error appears in the above-identified patent and that said Letters Patent is hereby corrected as shown below:

In the Specification

Column 7
Line 44, please delete "minor" and insert --mirror--

In the Claims

Column 10
Line 61, please delete "spectrometers" and insert --spectrometer--
Line 67, please delete "spectrometers" and insert --spectrometer--

Column 11
Line 2, please delete "pressures" and insert --pressure--

Signed and Sealed this
Eighteenth Day of April, 2017

Michelle K. Lee
*Director of the United States Patent and Trademark Office*